(12) United States Patent
Ganga, Sr.

(10) Patent No.: US 9,987,305 B1
(45) Date of Patent: *Jun. 5, 2018

(54) ANTIMICROBIAL SKIN CREAM

(71) Applicant: Yvon Samba Ganga, Sr., San Diego, CA (US)

(72) Inventor: Yvon Samba Ganga, Sr., San Diego, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/133,172

(22) Filed: Apr. 19, 2016

(51) Int. Cl.

| | | |
|---|---|---|
| *A61K 36/00* | (2006.01) |
| *A61K 33/06* | (2006.01) |
| *A61K 35/06* | (2006.01) |
| *A61K 31/185* | (2006.01) |
| *A61K 31/045* | (2006.01) |
| *A61K 33/04* | (2006.01) |
| *A61K 38/01* | (2006.01) |
| *A61K 36/63* | (2006.01) |
| *A61K 36/61* | (2006.01) |
| *A61K 36/82* | (2006.01) |
| *A61K 35/644* | (2015.01) |
| *A61K 36/886* | (2006.01) |
| *A61K 33/12* | (2006.01) |
| *A61K 31/355* | (2006.01) |
| *A61K 31/07* | (2006.01) |
| *A61K 31/525* | (2006.01) |
| *A61K 31/197* | (2006.01) |
| *A61K 31/4188* | (2006.01) |
| *A61K 31/675* | (2006.01) |
| *A61K 31/59* | (2006.01) |
| *A61K 9/06* | (2006.01) |
| *A61K 9/00* | (2006.01) |

(52) U.S. Cl.
CPC ............ *A61K 33/06* (2013.01); *A61K 9/0014* (2013.01); *A61K 9/06* (2013.01); *A61K 31/045* (2013.01); *A61K 31/07* (2013.01); *A61K 31/185* (2013.01); *A61K 31/197* (2013.01); *A61K 31/355* (2013.01); *A61K 31/4188* (2013.01); *A61K 31/525* (2013.01); *A61K 31/59* (2013.01); *A61K 31/675* (2013.01); *A61K 33/04* (2013.01); *A61K 33/12* (2013.01); *A61K 35/06* (2013.01); *A61K 35/644* (2013.01); *A61K 36/61* (2013.01); *A61K 36/63* (2013.01); *A61K 36/82* (2013.01); *A61K 36/886* (2013.01); *A61K 38/014* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 2002/0106337 A1* | 8/2002 | Deckers ................. | A23D 7/001 424/59 |
| 2010/0178511 A1* | 7/2010 | Letard ................... | C07F 15/025 428/404 |

FOREIGN PATENT DOCUMENTS

DE          10145833 A  *  3/2003

OTHER PUBLICATIONS

Angienda et al, Potential application of plant essential oils at sub-lethal concentrations under extrinsic conditions that enhance their antimicrobial effectiveness against pathogenic bacteria. African Journal of Microbiology Research (2010), vol. 4, No. 16, pp. 1678-1684.*

* cited by examiner

*Primary Examiner* — Qiuwen Mi
(74) *Attorney, Agent, or Firm* — Plager Schack LLP

(57) ABSTRACT

Some embodiments of the present disclosure include a cream for treating the skin. The cream may include gray clay kaolin; sodium lauryl ether sulfate; blue tartarzine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D. The cream may also include fatty acids.

8 Claims, No Drawings

ANTIMICROBIAL SKIN CREAM

BACKGROUND

The embodiments herein relate generally to skin care, and more particularly, to an antimicrobial skin cream.

The skin is the largest organ in the body, covering the surface of the human body and serving as the first line of defense in protecting the human from invasion of foreign pathogens and external injuries. In terms of wound healing, a human has the ability to self-heal a small area. However, when a person has a large area wound or poor skin restoration ability, such as those affected by diabetes, psoriasis, or leprosy, the individual may be unable to self-heal adequately, which can lead to infection.

Therefore, what is needed is a skin cream designed to improve tissue regeneration, particularly when treating skin lesions or wounds, while simultaneously having cosmetic applications as well.

SUMMARY

Some embodiments of the present disclosure include a cream for treating the skin. The cream may include gray clay kaolin; sodium lauryl ether sulfate; blue tartarzine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The cream of the present disclosure may be used to heal and rejuvenate the skin and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Gray clay kaolin
2. Sodium lauryl ether sulfate
3. Sodium chloride
4. Menthol
5. Water
6. Honey
7. Aloe Vera
8. Vitamins
9. Gelatin
10. Oils
11. Metabisulfite sodium
12. Talc
13. Green Tea The various elements of the cream of the present disclosure may be related in the following exemplary fashion. It is not intended to limit the scope or nature of the relationships between the various elements and the following examples are presented as illustrative examples only.

By way of example, some embodiments of the present disclosure include a skin cream comprising gray clay kaolin (chemical formula $Al_2Si_2O_5(OH)_4$); sodium lauryl ether sulfate; $CH_3(CH_2)_{11}(OCH_2CH_2)_nOSO_3Na$, wherein n is 2 or 3; blue tartrazine (chemical formula $C_{16}H_9N_4Na_3O_9S_2$); salt (NaCl); menthol ($C_{10}H_{20}O$); metabisulfite sodium ($Na_2S_2O_5$); gelatin; mineral oil ($C_{102}H_{151}O_{39}N_{31}$); olive oil ($CH_3(CH_2)_7CH=CH(CH_2)_7COOH$); oil of cloves

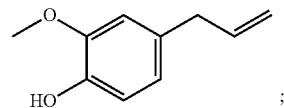

water; optionally, talc ($Mg_3Si_4O_{10}(OH)_2$); green tea; perfume, such as apple scented perfume; honey; aloe vera; optionally, oleic acid; optionally, benzoic acid; and optionally a mixture of vitamins. The fatty acids (oil of cloves, benzoic acid, and oleic acid) may have antimicrobial properties. In some embodiments, the mixture of vitamins may comprise vitamin E; vitamin D; vitamin C; vitamin B2; vitamin B5; vitamin H; vitamin B6; and vitamin D. Gray clay kaolin is a hydrous aluminum phylloscilicate and may include mineral elements, such as Fe, Mg, Na, K, Ti, Ca, and water. The $CH_3(CH_2)_{11}(OCH_2CH_2)_nOSO_3Na$ may provide for excellent decontamination, emulsification, dispersion, wetting, solubilizing performance and foaming. It may also function as a thickener with good solvency, while also having limited irritation to skin and eyes. The skin cream may have a pH of about 7.4. Additionally, the skin cream may be green in color.

A particular embodiment of the present disclosure may comprise a batch of the cream comprising about 240 kg gray kaolin clay, about 4 kg sodium lauryl ether sulfate, about 0.6 oz (or 18 g) blue tartrazine; about 2 kg salt, about 100 g menthol; about 50 g metabisulfite sodium; about 70 kg gelatin; about 20 L mineral oil; about 30 L olive oil; about 30 L oil of cloves; about 20 L water; about 20 kg talc; about 5 L green tea; about ⅛ L perfume; about 20 L honey; about 10 L aloe vera; about 2,000 international units (IU) vitamin E; about 100,000 IU vitamin A; about 300 mg vitamin C; about 100 mg vitamin B2; about 250 mg vitamin B5; about 2.5 mg vitamin H; about 100 mg vitamin B6; and about 400 IU vitamin D. In embodiments, the cream may comprise about 95% gray kaolin clay.

The gray clay kaolin may comprise alumina silicate, phosphate, calcium, magnesium, sodium, and potassium. The high silica content of the clay may result in the strengthening of the elastic tissues on the body, particularly in the case of contaminated blood.

The gelatin used in forming the cream of the present disclosure may be comprised mainly of collagen, which is a protein found in animal tissues, ligaments, tendons, bone, and skin. Thus, the gelatin may have healing properties, because it is a rich source of dietary collagen. The gelatin may also comprise proline, which is an amino acid that may help maintain a youthful appearance.

The blue tartrazine used in the cream may be a product derived from synthetic lemon yellow and is conventionally used as a food coloring.

The mineral oil included in the cream of the present disclosure may prevent water loss from the skin. In other words, it may act as a moisturizer. In some embodiments, the mineral oil may be replaced by Vaseline. The use of mineral oil may lead to an increase in stratum corneum content by reducing transepidermal and emoliency.

To summarize, the skin cream of the present disclosure may comprise the following:

Part 1: Gray clay kaolin

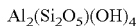

All elements listed in formula:
Al, H, O, Si—search for minerals with similar chemistry
Common Mineral Elements: Fe,Mg,Na,K,Ti,Ca,$H_2O$
$(Ca,Na,H)(Al,Mg,Fe,Zn)_2(Si,Al)_{4010}(OH)_2*H_2O+$

where
n is 2 or 3

Part 2: sodium laureth sulfate: $CH_3(CH_2)_{10}CH_2(OCH_2CH_2)OSO_3Na$

Part 3: water, which naturally contains minerals, such as Mg, Na, Ca, Fe, and the like Part 4: blue tartrazine ($C_{16}H_9N_{43}O_9S_2$):

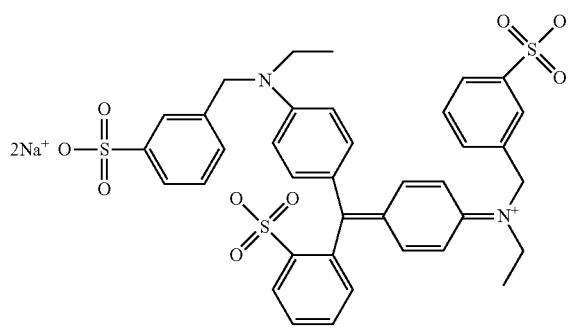 [SMILES: CCN(Cc1cccc(S(=O)(=O)O)c1)c1ccc(C(=C2C=CC(=[N+](CC)Cc3cccc(S(=O)(=O)O)c3)C=C2)c2ccccc2S(=O)(=O)O)cc1]

Final Product: $(Al,Zn,Fe1,67MgO,33)Si_{4010}(OH)_2Na^+Ca^{++})$

The weak acid character of the green clay as a Bronsted character clay arises mainly due to the dissociation of the intercalated water molecules coordinated to lauryl ether sulfate and blue tartrazine. Higher levels of Bronsted acidity are achieved when highly polarizing ions in solution have exchanged for $Na^+$, $Ca^{2+}$, in the natural clay, ions $Na^+$ present in laureth sulfate and blue tartrazine with alkali properties:

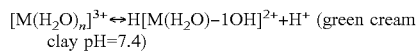

The surface area and the pore volume in the green cream clay structure may also add to the efficiency of the catalyst. Total acidity may be further increased by proton-exchange on treating the gray clay with water, sodium laureth sulfate, and blue tartrazine. As a result, a corrosive acid medium is avoided, and the clay is used as a Bronsted acid.

The interlayer in the antimicrobial green clay normally contains $Na^+$, $Ca^{2+}$, and $Mg^{2+}$ that are alkali properties as compensatory cations for the charge imbalance. When the clay is dry, these cations reside in the hexagonal cavities of the silica sheets. However, when the clay is treated with water, lauryl ether sulfate, and blue tratarzine, the cations may relocate themselves in the interlamellar region and become exchangeable by a variety of both metallic and non metallic cations, such as $H_3O^+$, $Al^{3+}$, $Fe^{3+}$ and the like.

The skin cream of the present disclosure may, therefore, comprise an antimicrobial, kaolinite and montmorillonite green cream clay composition with weak acids (fatty acids), oleic acids, benzoic acids, clove oil (C5, C14 antimicrobial properties and anti-aging abilities and properties), trace elements, vitamins, and mineral elements. The final skin cream may provide the ability and function of healing for the skin, wounds, and burns without spots or scars. In some embodiments, the cream may be used with poultice and compresses for burns and deep wounds.

The green tea in the cream of the present disclosure may help fight inflammation. The salt may have strong cleansing properties. The talc may be a mineral comprising hydrated magnesium silicate ($H_2Mg_3(SiO_3)$ or $Mg_3SiO_{10}(OH)_2$. The menthol ($C_{10}H_{19}OH$) may relieve minor aches and pains. Clove oil may be used for its antiseptic properties. Additionally, it contains eugenol, which has anti-bacterial properties; thus, the clove oil may help clear cystic acne and kill infections, thus reducing swelling. Olive oil may help fight signs of aging. The honey used in the cream of the present disclosure may be a saturated or super saturated solution of sugars. The honey may be diluted by wound exudates, creating hydrogen peroxide via a glucose oxidase enzyme reaction and resulting in antibacterial activity that does not damage the tissue.

The vitamins included in the cream may have various purposes. For example, vitamin A may help rebuild tissue by playing a role in the development of lymphocytes, which are cells that fight off bacteria and disease. Vitamin D may contain effective antioxidants that help fight free radicals in the body. Vitamin C may provide potent antioxidant protection, healing the skin from damage from free radicals, may boost healthy collagen production, may reduce the appearance of brown spots and other sun damage, may reduce inflammation and irritation, may fade post-breakout red marks, and may increase the effectiveness of sunscreens. Vitamins B2 may promote metabolism and mobilize iron from storage to incorporate into cells. Vitamin B6 may help utilize the energy contained in food and is important for carbohydrate, protein, and fat metabolism.

The cream of the present disclosure may have a clay-like consistency, wherein the ingredients of the cream may stimulate the regeneration of skin cells. Thus, facials masks and exfoliating scrubs made with the cream may result in the stem cells located within the skin actively generate differentiating cells that may ultimately form either the body surface or the hairs that emanate from it. The stem cells may be able to replenish themselves, continually rejuvenating the skin and hair.

In some embodiments, the cream may be synthesized using a 3-phase process: (1) creating an anti-microbial colloid liquid, which may be blue; (2) creating an anti-microbial solid, which may be green; and (3) creating an anti-microbial, creamy, gelatinous solid and vitamin, which may be green. Mixing of the cream may be done with a mixer coated with a plastic material. This specific type of mixer may be needed because the skin cream is rich in mineral elements, trace elements, weak acids, and vitamins. Examples of each step are described below.

Example 1: Creating the Anti-Microbial Colloid Liquid 2 kg of salt were mixed in a phase manner with water. Sodium lauryl ether sulfate and 0.6 oz (or 18 g) of blue tartrazine were mixed in with the salt water, creating the anti-microbial colloidal solution having a blue color.

Example 2: Creating the Anti-Microbial Solid

The colloidal blue anti-microbial solution prepared in Example 1 was mixed with 30 L olive oil; 30 L clove oil; 20 L honey; 5 L green tea; 10 L aloe vera; a 240 kg mixture comprising kaolin gray, phillosilicates, and aluminum silicate hydrates; 20 kg of talc; and 20 L of mineral oil. The solution was mixed thoroughly using a plastic coated blender, resulting in a green clay cream. It could have alternatively been mixed using just a plastic mixing spoon.

Example 3: Creating the Anti-Microbial, Creamy, Gelatinous Solid 75 kg of gelatin was slightly warmed to about 40° C. with 100 g of menthol to create a diluted solution. The amount of gelatin may be changed to change the viscosity of the skin cream. In embodiments, the gelatin may be added as a granular powder, which would swell when stirred into water. When dry gelatin is used, it may be used in an amount such that a water/gelatin mixture would not exceed about 34% gelatin. While warming, the gelatin solution may be allowed to hydrate for about 30 min. The diluted solution was poured into a mixing bowl. The green clay cream from Example 2 was then mixed into the mixing bowl. While the composition is being blended, it was simultaneously cooled to about 37° C. After cooling, vitamins are added to the mixture, which is then mixed again, creating antimicrobial green cream Kaolin clay, gelatinous and bright (the cream of the present disclosure).

The resulting cream includes silica, aluminum, calcium, and potassium as major elements and copper, lithium, molydedenum, and cobalt as minor elements. Some embodiments of the cream have a formula represented by $(Al,Zn,Fe_1,67MgO_{33})Si_4O_{10}(OH)_2Na^+Ca^{2+}$ plus weak acids, such as benzoic acid, fatty acids, such as scorbic acid, vitamins, and an antimicrobial agent. The mineral content of the product may vary due to the impurities.

The cream has anti-microbial and antibiotic properties and comprises trace elements, minerals, protein, polypeptides, and a weak acid, such as benzoic acid, which may give the cream its anti-aging and anti-microbial properties.

To use the cream of the present disclosure, a user may apply it externally on the skin or internally. When the cream is applied to the skin, transduction may occur, causing physical energy to be converted into energy used by the nervous system and reducing tension and anxiety in a user. For large wounds and burns, the cream may be gently rubbed on the wound or burn and covered with a compress when dry. The pain may be inhibited and the wound may heal without forming a scar. The cream may be removed from the body after the wound is healed by hydrotherapy, which may eliminate toxins.

The cream of the present disclosure may clean the skin of all or substantially all impurities, such as acne, spots, dead, skin fat, and the like. The cream may also have the ability to clean the face, heal most skin blemishes, whitlow, boils, ringworm, burns, stings, lesions, and the like. The cream may also be able to curb the proliferation of parasites, harmful bacteria, and microbes. The cream may also drain impurities, such as puss, from fabric, as the cream absorbs excess liquid and neutralizes the actions of various alkaloids. Moreover, the cream may have the ability to clean the blood and lymphatic system. The cream may also reinforce defenses, revitalize organs, neutralize poisons, strengthen bones, and reduce inflammation. In some embodiments, the cream may be used to nourish the scalp in cases of alopecia.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A cream for treating the skin, the cream comprising:
    gray clay kaolin;
    sodium lauryl ether sulfate; $CH_3(CH_2)_{11}(OCH_2CH_2)_n OSO_3Na$, where n is from about 2 to about 3;
    blue tartrazine, $C_{16}H_9N_{43}O_{92}S_2$;
    sodium chloride;
    menthol;
    metabisulfite sodium;
    gelatin;
    mineral oil;
    olive oil;
    oil of cloves;
    water;
    green tea;
    talc;
    honey; and
    aloe vera,
    wherein:
        a weight ratio of sodium lauryl sulfate to gray clay kaolin is about 1:60;
        a weight ratio of talc to gray clay kaolin is about 1:12; and
        a weight ratio of gelatin to gray clay kaolin is about 1:3.4.

2. The cream of claim 1, further comprising perfume.

3. The cream of claim 1, further comprising a mixture of vitamins.

4. The cream of claim 3, wherein the mixture of vitamins comprises vitamin E, vitamin C, vitamin B2, vitamin B5, vitamin H, vitamin B6, and vitamin D.

5. The cream of claim 1, further comprising apple perfume, vitamin E, vitamin D, vitamin C, vitamin B2, vitamin B5, vitamin H, vitamin B6, and vitamin D.

6. The cream of claim 5, wherein a batch of the cream comprises:
    about 240 kg gray kaolin clay;
    about 4 kg sodium lauryl ether sulfate;
    about 0.6 oz blue tartrazine;
    about 2 kg sodium chloride;
    about 100 g menthol;
    about 50 g metabisulfite sodium;
    about 75 kg gelatin;
    about 20 L mineral oil;
    about 30 L olive oil;
    about 30 L oil of cloves;
    about 20 L water;
    about 20 kg talc;
    about 5 L green tea;
    about ⅛ L perfume;
    about 20 L honey;
    about 10 L aloe vera;
    about 2,000 international units (IU) vitamin E;
    about 100,000 IU vitamin A;
    about 300 mg vitamin C;
    about 100 mg vitamin B2;
    about 250 mg vitamin B5;

about 2.5 mg vitamin H;
about 100 mg vitamin B6; and
about 400 IU vitamin D.

7. The cream of claim 1, wherein the cream comprises about 95% gray clay kaolin.

8. The cream of claim 1, wherein the cream has a pH of about 7.4.

* * * * *